US011547343B2

(12) United States Patent
Mahajan et al.

(10) Patent No.: US 11,547,343 B2
(45) Date of Patent: Jan. 10, 2023

(54) PVC ADJUSTED AF DETECTION

(71) Applicant: Cardiac Pacemakers, Inc., St. Paul, MN (US)

(72) Inventors: Deepa Mahajan, North Oaks, MN (US); David L. Perschbacher, Coon Rapids, MN (US); Sunipa Saha, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 152 days.

(21) Appl. No.: 16/845,552

(22) Filed: Apr. 10, 2020

(65) Prior Publication Data
US 2020/0323452 A1   Oct. 15, 2020

Related U.S. Application Data

(60) Provisional application No. 62/833,217, filed on Apr. 12, 2019.

(51) Int. Cl.
| | |
|---|---|
| A61B 5/361 | (2021.01) |
| A61B 5/00 | (2006.01) |
| A61B 5/024 | (2006.01) |
| A61B 5/363 | (2021.01) |
| A61B 5/364 | (2021.01) |

(52) U.S. Cl.
CPC ............ *A61B 5/361* (2021.01); *A61B 5/0022* (2013.01); *A61B 5/0024* (2013.01); *A61B 5/0031* (2013.01); *A61B 5/02416* (2013.01); *A61B 5/363* (2021.01); *A61B 5/364* (2021.01); *A61B 5/6802* (2013.01); *A61B 2562/0219* (2013.01); *A61B 2562/0247* (2013.01)

(58) Field of Classification Search
CPC ................................ A61B 5/361; A61B 5/364
USPC ......................................................... 600/518
See application file for complete search history.

(56) References Cited

U.S. PATENT DOCUMENTS

| | | | |
|---|---|---|---|
| 8,560,058 B2 | 10/2013 | Babaeizadeh et al. | |
| 9,999,368 B2 | 6/2018 | Perschbacher et al. | |
| 2006/0195037 A1 | 8/2006 | Wiesel | |
| 2010/0114203 A1 | 5/2010 | Burnes et al. | |
| 2011/0125206 A1* | 5/2011 | Bornzin | A61B 5/0031 607/5 |
| 2014/0330134 A1 | 11/2014 | Chon et al. | |
| 2015/0342466 A1 | 12/2015 | Thakur et al. | |
| 2016/0045125 A1 | 2/2016 | Krueger et al. | |
| 2017/0127965 A1 | 5/2017 | Krueger et al. | |
| 2017/0290550 A1* | 10/2017 | Perschbacher | A61B 5/364 |
| 2017/0296076 A1* | 10/2017 | Mahajan | A61N 1/37 |

(Continued)

OTHER PUBLICATIONS

"U.S. Appl. No. 16/845,578, Examiner Interview Summary dated May 9, 2022", 3 pgs.

(Continued)

*Primary Examiner* — Nicole F Lavert
*Assistant Examiner* — Nicole F Johnson
(74) *Attorney, Agent, or Firm* — Schwegman Lundberg & Woessner, P.A.

(57) ABSTRACT

This document discusses, among other things, systems and methods to receive cardiac electrical information and premature ventricular contraction (PVC) information of a subject, detect atrial fibrillation (AF) of the subject using the received cardiac electrical information, and adjust AF detection using the received PVC information.

20 Claims, 5 Drawing Sheets

(56) References Cited

U.S. PATENT DOCUMENTS

2018/0028086 A1 2/2018 Cao et al.
2018/0192902 A1 7/2018 Perschbacher et al.
2020/0323459 A1 10/2020 Saha et al.

OTHER PUBLICATIONS

"U.S. Appl. No. 16/845,578, Non Final Office Action dated Apr. 12, 2022", 12 pgs.
"U.S. Appl. No. 16/845,578, Response filed Jul. 12, 22 to Non Final Office Action dated Apr. 12, 2022", 17 pgs.

* cited by examiner

PVC ADJUSTED AF DETECTION

CLAIM OF PRIORITY

This application claims the benefit of priority under 35 U.S.C. § 119(e) of U.S. Provisional Patent Application Ser. No. 62/833,217, filed on Apr. 12, 2019, which is herein incorporated by reference in its entirety.

TECHNICAL FIELD

This document relates generally to medical devices, and more particularly, but not by way of limitation, to systems, devices, and methods for adjusting atrial fibrillation (AF) detection or classification using premature ventricular contraction (PVC) information.

BACKGROUND

Heart failure (HF) is a reduction in the ability of the heart to deliver enough blood to meet bodily needs. HF patients commonly have enlarged heart with weakened cardiac muscles, resulting in reduced contractility and poor cardiac output of blood. Signs of HF include pulmonary congestion, edema, difficulty breathing, etc. HF is often a chronic condition, but can also occur suddenly, affecting the left, right, or both sides of a heart. Causes of HF include, among others, coronary artery disease, myocardial infarction, high blood pressure, atrial fibrillation, valvular heart disease, alcoholism, infection, cardiomyopathy, or one or more other conditions leading to a decreased pumping efficiency of the heart.

An arrhythmia is an abnormal heart rhythm, or any heart rhythm (e.g., fast, slow, irregular, etc.) that is not a normal heart rhythm. Arrhythmias include, among others: bradycardia; tachycardia; premature, extra, or skipped heart beats; heart defects; and atrial or ventricular fibrillation affecting one or more chambers of the heart. Atrial fibrillation (AF) is as an abnormal heart rhythm characterized by rapid and irregular activity in the left or right atria of the heart. AF is commonly associated with a reduction in cardiac output, an increased risk of heart failure (HF), dementia, and stroke. Risk factors for AF include, among others, high blood pressure, heart failure (HF), valvular heart disease, COPD, obesity, and sleep apnea.

Premature ventricular contractions (PVCs) (also referred to as premature ventricular complexes, ventricular premature beats, or ventricular extrasystoles or palpitations) are premature or extra heartbeats that begin in the left or right ventricles of the heart, often originating sooner than the next expected heartbeat, disrupting a normal heart rhythm that originates in the sinoatrial (SA) node in the right atrium of the heart. PVCs are often associated with injury to the heart muscle, such as from coronary artery disease, congenital heart disease, high blood pressure, or HF.

An ambulatory medical device (AMD), such as an implantable, wearable, or other external medical device, can be configured to monitor, detect, or treat various conditions, including HF, arrhythmias, etc.

SUMMARY

This document discusses, among other things, systems and methods to receive cardiac electrical information and premature ventricular contraction (PVC) information of a subject, detect atrial fibrillation (AF) of the subject using the received cardiac electrical information, and adjust AF detection using the received PVC information.

The system can include a signal receiver circuit configured to receive the cardiac electrical information and PVC information of the subject, and an assessment circuit configured to detect AF of the subject using the received cardiac electrical information, and determine a PVC state of the subject using a count of PVC events in a first detection window, including: if the PVC event count is below a first threshold, determine a low-PVC state; and if the PVC event count meets or exceeds the first threshold, determine a high-PVC state. The assessment circuit can be configured to adjust the AF detection using the determined PVC state, including: detect AF of the subject using a low-PVC burden mode in the low-PVC state; and detect AF of the subject using a high-PVC burden mode in the high-PVC state, wherein an AF detection threshold is different in the high-PVC burden mode than in the low-PVC burden mode. In an example, the AF detection criteria can include whether or not a PVC event is included or excluded from the first detection window, or one or more other AF or PVC detection parameters.

Example 1 is a system, comprising: a signal receiver circuit configured to receive cardiac electrical information and premature ventricular contraction (PVC) information of a subject; and an assessment circuit configured to: detect atrial fibrillation (AF) of the subject using the received cardiac electrical information; and adjust the AF detection using the received PVC information.

In Example 2, the subject matter of Example 1 optionally includes wherein the assessment circuit is configured to determine a PVC state of the subject using the received PVC information and to adjust AF detection using the determined PVC state.

In Example 3, the subject matter of Example 2 optionally includes wherein the assessment circuit is configured to detect a PVC event using the received PVC information and to count detected PVC events in a first detection window.

In Example 4, the subject matter of Example 3 optionally includes wherein the assessment circuit is configured to determine the PVC state of the subject and to adjust the AF detection using the count of PVC events in the first detection window.

In Example 5, the subject matter of any one or more of Examples 3-4 optionally include wherein the received PVC information comprises an indication of a detected PVC event.

In Example 6, the subject matter of any one or more of Examples 3-5 optionally include wherein, if the PVC event count is below a first threshold, the assessment circuit is configured to determine a low-PVC state, and the system is configured to detect AF of the subject using a low-PVC burden mode, and wherein, if the PVC event count meets or exceeds the first threshold, the medial-device system is configured to determine a high-PVC state, and the system is configured to detect AF of the subject using a high-PVC burden mode.

In Example 7, the subject matter of Example 6 optionally includes wherein the assessment circuit is configured to detect AF in the first detection window using the received cardiac electrical information in the first detection window, wherein, to adjust the AF detection in the high-PVC burden mode, the assessment circuit is configured to remove detected PVC events from the first detection window.

In Example 8, the subject matter of Example 7 optionally includes wherein, to adjust the AF detection in the high-PVC burden mode, the assessment circuit is configured to remove detected PVC events, and cardiac electrical information from an interval at least one of preceding or proceeding the detected PVC events from the first detection window.

In Example 9, the subject matter of any one or more of Examples 3-8 optionally include wherein, if the PVC event count is below a first threshold, the assessment circuit is configured to determine a low-PVC state, and the assessment circuit is configured to detect AF of the subject using a low-PVC burden mode, wherein, if the PVC event count meets or exceeds the first threshold, but is below a second threshold higher than the first threshold, the medial-device system is configured to determine a high-PVC state, and the assessment is configured to detect AF of the subject using a high-PVC burden mode, and wherein, if the PVC event count meets or exceeds the second threshold, the system is configured to suspend AF detection.

In Example 10, the subject matter of any one or more of Examples 1-9 optionally include wherein the assessment circuit is configured to control storage of received cardiac electrical information using the received PVC information.

Example 11 is a method, comprising: receiving cardiac electrical information and premature ventricular contraction (PVC) information of a subject using a signal receiver circuit; detecting, using an assessment circuit, atrial fibrillation (AF) of the subject using the received cardiac electrical information; and adjusting, using the assessment circuit, AF detection using the received PVC information.

In Example 12, the subject matter of Example 11 optionally includes determining, using the assessment circuit, a PVC state of the subject using a count of PVC events in a first detection window.

In Example 13, the subject matter of any one or more of Examples 11-12 optionally include detecting, using the assessment circuit, a PVC event using the received PVC information; counting, using the assessment circuit, detected PVC events in a first detection window; and determining, using the assessment circuit, a PVC state of the subject using the count of PVC events in the first detection window, wherein adjusting AF detection comprises using the determined PVC state.

In Example 14, the subject matter of Example 13 optionally includes wherein determining the PVC state of the subject comprises determining: a low-PVC state if the PVC event count is below a first threshold; and a high-PVC state if the PVC event count meets or exceeds the first threshold, but is below a second threshold, and wherein detecting AF of the subject includes using: a low-PVC burden mode if the PVC event count is below the first threshold; and a high-PVC burden mode if the PVC event count meets or exceeds the first threshold, but is below the second threshold.

In Example 15, the subject matter of Example 14 optionally includes suspending AF detection if the PVC event count meets or exceeds the second threshold higher than the first threshold.

In Example 16, the subject matter of any one or more of Examples 14-15 optionally include wherein detecting AF comprises detecting an AF episode in the first detection window using the received cardiac electrical information in the first detection window, and wherein, in the high-PVC burden mode, adjusting AF detection comprises removing detected PVC events from the detection window and detecting AF using the remaining cardiac electrical information in the first detection window.

In Example 17, the subject matter of Example 16 optionally includes wherein, in the high-PVC burden mode, adjusting AF detection comprises removing detected PVC events and cardiac electrical information from an interval at least one of preceding or proceeding the detected PVC events from the first detection window.

Example 18 is a system, comprising: a signal receiver circuit configured to receive cardiac electrical information and premature ventricular contraction (PVC) information of a subject; and an assessment circuit configured to: detect atrial fibrillation (AF) of the subject using the received cardiac electrical information of the subject; determine a PVC state of the subject using a count of PVC events in a first detection window, including: if the PVC event count is below a first threshold, determine a low-PVC state; and if the PVC event count meets or exceeds the first threshold, determine a high-PVC state; and adjust the AF detection using the determined PVC state, including: detect AF of the subject using a low-PVC burden mode in the low-PVC state; and detect AF of the subject using a high-PVC burden mode in the high-PVC state, wherein an AF detection threshold is different in the high-PVC burden mode than in the low-PVC burden mode.

In Example 19, the subject matter of Example 18 optionally includes wherein the assessment circuit is configured to suspend atrial fibrillation detection if the PVC event count meets or exceeds a second threshold higher than the first threshold.

In Example 20, the subject matter of any one or more of Examples 18-19 optionally include wherein the assessment circuit is configured to detect AF in the first detection window using the received cardiac electrical information in the first detection window, wherein, to adjust the AF detection in the high-PVC burden mode, the assessment circuit is configured to remove detected PVC events and cardiac electrical information from an interval at least one of preceding or proceeding the detected PVC events from the first detection window.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, systems and methods to adjust atrial fibrillation (AF) detection to account for the occurrence of premature ventricular contractions (PVCs), such as using detected PVC events or PVC information to adjust one or more AF detection parameters, in certain examples, increasing the robustness of AF detection for the subject.

PVC events include mis-timed, "premature" events, often falsely detected as, or contributing to the false detection of, an AF event. Existing AF detection or classification can account for a number or rate of PVC events; however, they do not adequately tolerate above-average occurrences of PVCs, but generally attempt to distinguish PVC events from irregular rhythms, such as AF.

The present inventors have recognized, among other things, that in certain examples, such as the number or rate of PVC events is below a first threshold, it can be advantageous to not discriminate or distinguish PVC events, but to proceed with AF detection on all valid beats or intervals within a detection window. When the number or rate of PVC events increases above the first threshold, such between first and second thresholds, it can be advantageous to discriminate or distinguish PVC events, in certain examples, removing them from the detection window. In an example, otherwise valid beats or intervals preceding, proceeding, or both preceding and proceeding a detected PVC event can be removed from the detection window with the PVC event. In an example, when the number or rate of PVC events increases above the second threshold, AF detection can cease and a user may be informed. In other examples, more or less thresholds can be used, increasing the number of zones or sub-zones of AF or PVC detection adjustment.

Examples of AF detection algorithms can be found, for example, in the commonly assigned Krueger et al. U.S. patent application Ser. No. 14/825,669, titled "Atrial Fibrillation Detection Using Ventricular Rate Variability" (herein, "the '669 application"); Perschbacher et al. U.S. patent application Ser. No. 15/082,440, titled "Atrial Fibrillation Detection" (herein, "the '440 application"); Krueger et al. U.S. patent application Ser. No. 15/341,565, titled "Method and Apparatus for Enhancing Ventricular Based Atrial Fibrillation Detection Using Atrial Activity" (herein, "the '565 application"); and Perschbacher et al. U.S. patent application Ser. No. 15/864,953, titled "Atrial Fibrillation Discrimination Using Heart Rate Clustering" (herein, "the '953 application"), each of which are hereby incorporated by reference in their entireties, including their disclosure of AF detection and AF detection algorithms including, for example: AF detection using pairs of ventricular information detected from a ventricle, including rate changes and rate change characteristics, and determination of valid heart beats or intervals using various characteristics, including threshold rates, intervals, morphology criterion, etc., such as disclosed in the '669 application; AF detection using a distribution of ventricular depolarization intervals, such as disclosed in the '440 application; AF detection using atrial activity scores from an atrial detection window prior to a detected ventricular polarization, such as disclosed in the '565 application; AF discrimination using clustered depolarization information, such as disclosed in the '953 application, etc.

The present inventors have recognized, among other things, that an AF detection algorithm for a subject can be automatically adjusted using a determined PVC burden of the subject. For example, the PVC burden can be determined and categorized using a number of PVC events (or candidate PVC events) detected in a specified time window, in a specified number of cardiac intervals, a specified number of valid cardiac intervals, etc. In other examples, the PVC burden can be determined and categorized using a rate of PVC events (or candidate PVC events) to non-PVC events, etc. PVC events (or candidate PVC events) can be detected using one or more PVC detection criteria. The PVC burden can be scored, categorized, etc., and used to adjust one or more AF detection algorithms, such as one or more parameters of the one or more AF detection algorithms. Adjustments can include, for example, the cardiac electrical information (e.g., specific beats or intervals from a detection window, etc.) considered or removed for AF detection. For example, if the PVC burden is high, cardiac electrical information indicative of a PVC event can be removed from a detection window, and non-PVC events, or events below a PVC threshold or measure, can be considered. In other examples, cardiac electrical information preceding, proceeding, or both preceding and proceeding (e.g., one or more specific beats or intervals before, after, or before and after a PVC event, etc.) can be removed from consideration. Moreover, specific PVC detection criteria can be adjusted between or within the different determined PVC burdens. For example, as the PVC burden increases, the criteria used to determine a PVC event (e.g., frequency, morphology, timing, amplitude, etc.) can become less exclusive to account for the higher probability of the PVC event.

In an example, the PVC burden can be categorized, such as in one or more categories (e.g., low and high; low, high, and very high; first-fourth; etc.). In an example, a low PVC burden can include a normal burden, such as an expected PVC burden that one or more of the example AF detection algorithms above are designed to tolerate without interruption or suspension, etc. One or more additional PVC burdens beyond the low PVC burden can be determined, such as high and very-high PVC burdens, etc., and the one or more AF detection algorithms can be adjusted according to the determined one or more additional PVC burdens.

In certain examples, AF detection can include detection windows, such as measured by one or more of time (e.g., 30-second windows, 2-minute windows, or one or more other time periods, etc.), cardiac intervals (e.g., a number of cardiac intervals, etc.), valid cardiac intervals (e.g., within one or more time boundaries (ms), such as above a low threshold, below a high threshold; a change from one or more previous or average intervals; etc.), etc.

In an example, the low PVC burden can include a determined PVC burden below a first threshold (e.g., 30% of the beats (or valid beats) in a detection window, etc.). A high PVC burden can include a determined PVC burden above the first threshold, and in certain examples, below a second threshold (e.g., 70% of the beats (or valid beats) in the detection window, etc.). A very-high PVC burden can include a determined PVC burden above the second threshold. In other examples, one or more other percentages, ranges, or number or levels of categories can be used. In certain examples, such as depending on the robustness of the AF detection algorithm, or desired sensitivity or specificity, the first threshold can range between 10% and 50%, and the second threshold can range between 50% and 90%. In an example, only a first threshold can be used (e.g. between 10 and 90%), defining two zones. In other examples, three or more threshold can be used, defining 4 or more zones with different ranges or boundaries, etc.

In an example, when the low PVC burden is determined, a first AF detection algorithm, or a first set of AF parameters, can be used to detect or categorize AF in the subject. When the high PVC burden is determined, a second detection algorithm or set of AF parameters tuned to tolerate a higher number or rate of PVC events can be used to detect or classify AF in the subject. When the very-high PVC burden is determined, AF detection and/or classification can be suspended. In an example, as mentioned above, first and second thresholds can be positioned at 30% and 70%, respectively, or in other examples, at one or more other thresholds defining a number of ranges, etc. In certain examples, adjustments to the AF detection and/or classification using the determined PVC burden may increase sensitivity or specificity of AF or PVC detection, or avoid mis-detection or mis-classification. Increased sensitivity or specificity of detection can increase data collection and storage efficiency, providing a more robust patient monitoring system, in certain examples, using less storage or data processing than existing systems.

In certain examples, storage decisions can be made depending on the determined PVC burden. For example, AF detection windows or sub-windows can be stored including PVCs, such as for subsequent review, while non-PVC detection windows or sub-windows can be discarded and not stored. Varying device operation with determined PVC burdens can also save power, extending device lifespan. For example, AF detection can cease for a time period following a determined very-high PVC burden. In certain examples, an alert corresponding to the determined very-high PVC burden can be provided. AF detection can resume after a period of time (e.g., 10 minutes, 30 minutes, 1 hour, 6 hours, 12 hours, 1 day, etc.), in response to one or more triggers (e.g., a change in a state of the subject, a percentage change in heart rate, a change in posture, etc.). In other examples, the frequency of AF detection can be adjusted for a period following determination of a very-high PVC burden.

Moreover, improved detection or classification of AF in sophisticated, regulatory-compliant medical systems, components, or machinery may increase the efficiency of medical system resources, improving the functioning of modern regulated technological systems and methods not capable of being performed or managed by generic computers, components, or machinery.

Ambulatory medical devices (AMDs), including implantable or wearable medical devices, can be configured to monitor, detect, or treat various cardiac conditions associated with a reduced ability of a heart to sufficiently deliver blood to a body, such HF, arrhythmias, hypertension, etc. An AMD can include a single device or a plurality of medical devices or monitors implanted in a subject's body or otherwise positioned on or about the subject to monitor subject physiologic information of the subject, such as heart sounds, respiration (e.g., respiration rate, tidal volume, etc.), impedance (e.g., thoracic impedance, cardiac impedance, etc.), pressure (e.g., blood pressure), cardiac activity (e.g., heart rate), physical activity, posture, plethysmography, or one or more other physiologic parameters of a subject, or to provide electrical stimulation or one or more other therapies or treatments to optimize or control contractions of the heart.

In an example, the AMD can include one or more of: a respiration sensor configured to receive respiration information (e.g., a respiration rate (RR), a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); or one or more other sensors configured to receive physiologic information of the subject.

Traditional cardiac rhythm management (CRM) devices, such as pacemakers, defibrillators, or cardiac resynchronizers, include subcutaneous devices configured to be implanted in a chest of a subject, having one or more leads to position one or more electrodes or other sensors at various locations in or near the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the subject.

Implantable devices can additionally include leadless cardiac pacemakers (LCP), small (e.g., smaller than traditional implantable CRM devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Wearable or external medical sensors or devices can be configured to detect or monitor physiologic information of the subject without required implant or an in-patient procedure for placement, battery replacement, or repair. However, such sensors and devices, in contrast to implantable medical devices, may have reduced patient compliance, increased detection noise, or reduced detection sensitivity.

For each ambulatory medical device (AMD) described above (e.g., implantable medical device (IMD) or wearable medical devices (WHIM)), each additional sensor can increase system cost and complexity, reduce system reliability, or increase the power consumption and reduce the usable life of the ambulatory device. Accordingly, it can be beneficial to use a single sensor to determine multiple types of physiologic information, or a smaller number of sensors to measure a larger number of different types of physiologic information.

In an example, an accelerometer, microphone, or acoustic sensor can sense or detect acceleration information of the subject including or indicative of cardiac acceleration information (e.g., heart sound information, such as from pressure waveforms due to cardiac vibrations; endocardial acceleration information, such as from acceleration information detected on or within a cardiac chamber; cardiac vibration information; etc.) of the subject. In certain examples, the same or different accelerometer, microphone, acoustic sensor or one or more other activity, posture, or exertion sensors can receive exertion information (e.g., activity information, posture information, etc.) of the subject. Exertion information can include physical activity information of the subject occurring at a different frequency than cardiac acceleration information. Accordingly, the sampling rate to detect physical activity information of the subject is often much lower than that required to detect cardiac acceleration information (e.g., exertion is often detected at a sampling rate of 50 Hz or less, whereas cardiac acceleration information is often detected at a sampling rate of 1 kHz or higher).

In an example, a single sensor can detect acceleration information at a detection period and sampling rate such that both cardiac acceleration information and exertional information can be determined from the detected acceleration information over the same or overlapping time periods. However, such determination of the separate cardiac acceleration information and the exertion information from the same acceleration information can require substantial processing time and resources. Accordingly, when a single sensor is used to detect cardiac acceleration information and exertion information, the cardiac acceleration information and the exertion information are more often detected in non-overlapping time periods (e.g., the single sensor detects one of the cardiac acceleration information or the exertional information at a time) at different sampling rates and with different pre-processing (e.g., filters, signal conditioning, etc.), such as to reduce the processing resources required to sense and process the separate information in the AMD or medical-device system having limited or different storage, processing, power, and performance capabilities.

In other examples, different sensors (or a single sensor with different physical sensing portions or components) can be used to detect the cardiac acceleration information and the exertion information. For example, it can be advantageous to detect physical activity or exertion information using a more rigid sensor tuned to sense activity having a higher magnitude and lower frequency response than cardiac acceleration information; whereas it can be advantageous to detect cardiac acceleration information using sensor having higher sensitivity and sampling frequency (e.g., a microphone instead of an accelerometer, etc.). In certain examples, separate axes of a multi-axis sensor can be used to detect different information at different sampling rates.

Figure 1:
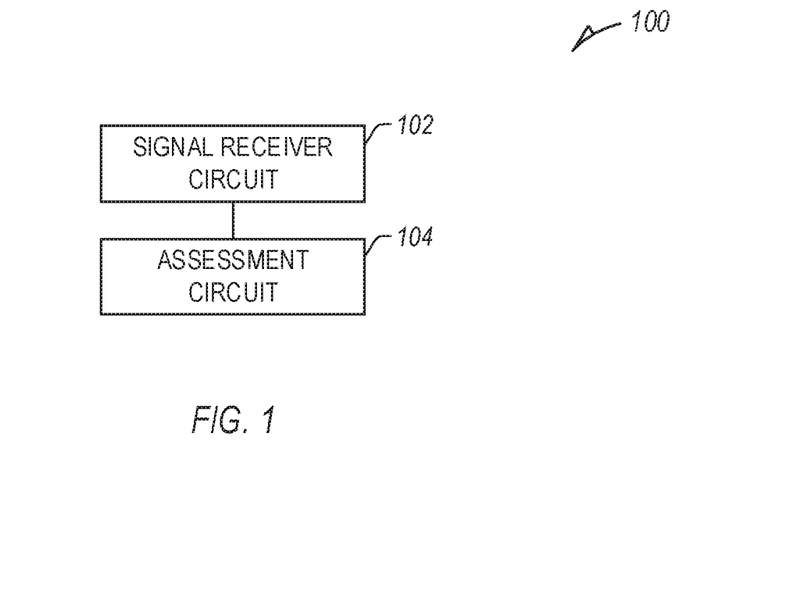
FIG. 1 illustrates an example medical-device system including a signal receiver circuit and an assessment circuit.

FIG. 1 illustrates an example system (e.g., a medical device, etc.) 100 including a signal receiver circuit 102 and an assessment circuit 104, each having an input and an output. The signal receiver circuit 102 can be configured to receive subject information, such as physiologic information of a subject, a patient (or a group of subjects or patients) from one or more sensors. In an example, the signal receiver circuit can be configured to receive cardiac electrical information of the subject, such as from a cardiac sensor (e.g., including one or more electrodes configured to sense electrical activity of the subject, such as cardiac electrical activity, and an amplifier configured to amplify the received cardiac electrical activity, etc.) or one or more other devices or sensors, etc. In an example, the signal receiver circuit can be configured to receive premature ventricular contraction (PVC) information of the subject, such as from one or more other devices or sensors. In an example, the system can include a PVC determination circuit configured to receive cardiac electrical information and to determine one or more PVC events using the received cardiac electrical information (e.g., using a timing, a morphology, a frequency, etc. of the cardiac electrical information, etc.).

The assessment circuit 104 can be configured to receive information from the signal receiver circuit 102, and to determine one or more parameters (e.g., composite physiologic parameters, stratifiers, one or more pacing parameters, etc.), such as described herein. In an example, the assessment circuit 104 can be configured to detect atrial fibrillation (AF) of the subject, such as an AF event or a potential AF event of the subject, using the received cardiac electrical information. In an example, the assessment circuit 104 can be configured to adjust the AF detection using the received PVC information.

The assessment circuit 104 can be configured to determine a subject condition, or an indication, risk, or stratification of worsening subject condition, using the received information. The assessment circuit 104 can provide acute or chronic monitoring of the subject condition, and in certain examples can be configured to provide an output to a user, such as a score, an alert, a trend, or indication to the subject or a clinician. In certain examples, the assessment circuit 104 can be configured to provide an indication that the subject seek medical treatment or be hospitalized in response to a determined change, or otherwise determine one or more therapy parameters, such as to be provided to a clinician for consideration, or to propose, control, or otherwise manage one or more therapies to the subject or one or more functions, modes, or operations of one or more components of a medical-device system. In other examples, the assessment circuit 104 can be configured to provide an output to another circuit, machine, or process, such as to control, adjust, or cease a therapy of a medical device, a drug delivery system, etc., or otherwise alter one or more processes or functions of a medical-device system.

Figure 2:
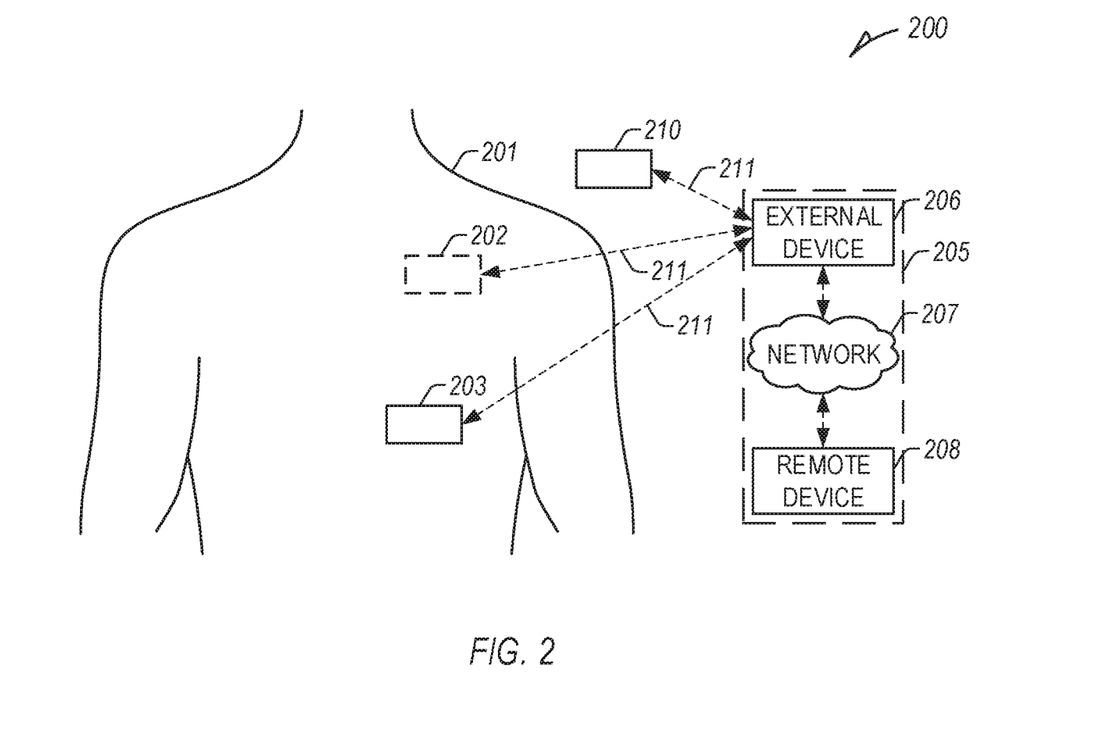
FIG. 2 illustrates an example patient management system and portions of an environment in which the system may operate.

FIG. 2 illustrates an example patient management system 200 and portions of an environment in which the system 200 may operate. The patient management system 200 can perform a range of activities, including remote patient monitoring and diagnosis of a disease condition. Such activities can be performed proximal to a patient 201, such as in a patient home or office, through a centralized server, such as in a hospital, clinic, or physician office, or through a remote workstation, such as a secure wireless mobile computing device.

The patient management system 200 can include one or more ambulatory devices, an external system 205, and a communication link 211 providing for communication between the one or more ambulatory devices and the external system 205. The one or more ambulatory devices can include an implantable medical device (IMB) 202, a wearable medical device 203, or one or more other implantable, leadless, subcutaneous, external, wearable, or ambulatory medical devices configured to monitor, sense, or detect information from, determine physiologic information about, or provide one or more therapies to treat various cardiac conditions of the patient 201, such as high blood pressure, an ability of a heart to sufficiently deliver blood to a body, including atrial fibrillation (AF), congestive heart failure (CHF), hypertension, or one or more other cardiac or non-cardiac conditions (e.g., dehydration, hemorrhage, renal dysfunction, etc.).

In an example, the IMB 202 can include one or more traditional cardiac rhythm management (CRM) devices, such as a pacemaker or defibrillator, implanted in a chest of a subject, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the subject 201. In another example, the IMD 202 can include a monitor implanted, for example, subcutaneously in the chest of subject 201.

The IMB 202 can include an assessment circuit configured to detect or determine specific physiologic information of the subject 201, or to determine one or more conditions or provide information or an alert to a user, such as the subject 201 (e.g., a patient), a clinician, or one or more other caregivers. The IMD 202 can alternatively or additionally be configured as a therapeutic device configured to treat one or more medical conditions of the subject 201. The therapy can be delivered to the subject 201 via the lead system and associated electrodes or using one or more other delivery mechanisms. The therapy can include anti-arrhythmic therapy to treat an arrhythmia or to treat or control one or more complications from arrhythmias, such as syncope, congestive heart failure (CHF), or stroke, among others. In other examples, the therapy can include delivery of one or more drugs to the subject 201 using the IMD 202 or one or more of the other ambulatory devices. Examples of the anti-arrhythmic therapy include pacing, cardioversion, defibrillation, neuromodulation, drug therapies, or biological therapies, among other types of therapies. In other examples, therapies can include cardiac resynchronization therapy (CRT) for rectifying dyssynchrony and improving cardiac function in CHF patients. In some examples, the IMD 202 can include a drug delivery system, such as a drug infusion pump to deliver drugs to the patient for managing arrhythmias or complications from arrhythmias, hypertension, or one or more other physiologic conditions. In yet other examples, the IMD 202 can include a therapy circuit or module configured to treat hypertension (e.g., a neurostimulation therapy circuit, a drug delivery therapy circuit, a stimulation therapy circuit, etc.).

The wearable medical device 203 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.). In other examples, the wearable medical device 203 can include an acoustic sensor or accelerometer to detect acoustic information (e.g., heart sounds) or the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc.

The patient management system 200 can include, among other things, a respiration sensor configured to receive respiration information (e.g., a respiration rate (RR), a respiration volume (tidal volume), etc.), a heart sound sensor configured to receive heart sound information, a thoracic impedance sensor configured to receive impedance information, a cardiac sensor configured to receive cardiac electrical information, an activity sensor configured to receive information about a physical motion (e.g., activity, posture, etc.), a plethysmography sensor, or one or more other sensors configured to receive physiologic information of the subject 201.

The external system 205 can include a dedicated hardware/software system, such as a programmer, a remote server-based patient management system, or alternatively a system defined predominantly by software running on a standard personal computer. The external system 205 can manage the subject 201 through the IMB 202 or one or more other ambulatory devices connected to the external system 205 via a communication link 211. In other examples, the IMB 202 can be connected to the wearable device 203, or the wearable device 203 can be connected to the external system 205, via the communication link 211. This can include, for example, programming the IMB 202 to perform one or more of acquiring physiological data, performing at least one self-diagnostic test (e.g., a device operational status, etc.), analyzing the physiological data to detect a cardiac arrhythmia, or optionally delivering or adjusting a therapy to the subject 201. Additionally, the external system 205 can send information to, or receive information from, the IMD 202 or the wearable device 203 via the communication link 211. Examples of the information can include real-time or stored physiological data from the subject 201, diagnostic data, such as detection of cardiac arrhythmias or events of worsening heart failure, responses to therapies delivered to the subject 201, or device operational status of the IMD 202 or the wearable device 203 (e.g., battery status, lead impedance, etc.). The communication link 211 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

By way of example and not limitation, the external system 205 can include an external device 206 in proximity of the one or more ambulatory devices, and a remote device 208 in a location relatively distant from the one or more ambulatory devices, in communication with the external device 206 via a communication network 207. Examples of the external device 206 can include a medical device programmer.

The remote device 208 can be configured to evaluate collected subject or patient information and provide alert notifications, among other possible functions. In an example, the remote device 208 can include a centralized server acting as a central hub for collected data storage and analysis. The server can be configured as a uni-, multi-, or distributed computing and processing system. The remote device 208 can receive data from multiple subjects or patients. The data can be collected by the one or more ambulatory devices, among other data acquisition sensors or devices associated with the subject 201. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory devices, such as the IMB. By way of example, alert notifications can include a Web page update, phone or pager call, E-mail, SMS, text or "Instant" message, as well as a message to the subject or patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiological data associated with the detected medical event to physiological data associated with the historical alerts.

The remote device 208 may additionally include one or more locally configured clients or remote clients securely connected over the communication network 207 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 208, including the server and the interconnected clients, may also execute a follow-up scheme by sending follow-up requests to the one or more ambulatory devices, or by sending a message or other communication to the subject 201 (e.g., the patient), clinician or authorized third party as a compliance notification.

The communication network 207 can provide wired or wireless interconnectivity. In an example, the communication network 207 can be based on the Transmission Control Protocol/Internet Protocol (TCP/IP) network communication specification, although other types or combinations of networking implementations are possible. Similarly, other network topologies and arrangements are possible.

One or more of the external device 206 or the remote device 208 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 206 or the remote device 208 can include a respective display unit for displaying the physiological or functional signals, or alerts, alarms, emergency calls, or other forms of warnings to signal the detection of arrhythmias. In some examples, the external system 205 can include an external data processor configured to analyze the physiological or functional signals received by the one or more ambulatory devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory devices or the external system 205 can be implemented using hardware, software, firmware, or combinations thereof. Portions of the one or more ambulatory devices or the external system 205 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The patient management system 200 can include a therapy device, such as a drug delivery device configured to provide therapy or therapy information (e.g., dosage information, etc.) to the subject 201, such as using information from one or more of the ambulatory devices. In other examples, one or more of the ambulatory devices can be configured to provide therapy or therapy information to the subject 201. The therapy device can be configured to send information to or receive information from one or more of the ambulatory devices or the external system 205 using the communication link 211. In an example, the one or more ambulatory devices, the external device 206, or the remote device 208 can be configured to control one or more parameters of the therapy device 210.

The external system 205 can allow for programming the one or more ambulatory devices and can receives information about one or more signals acquired by the one or more ambulatory devices, such as can be received via a communication link 211. The external system 205 can include a local external IMD programmer. The external system 205 can include a remote patient management system that can monitor patient status or adjust one or more therapies, such as from a remote location.

In various examples, the assessment circuit may be implemented using one or more of the IMD 202, the wearable medical device 203, or at the external system 205, such as using data extracted from the one or more ambulatory devices or data stored in a memory within the external system 205. In other examples, portions of the assessment circuit may be distributed between the one or more ambulatory devices and the external system 205.

Figure 3:
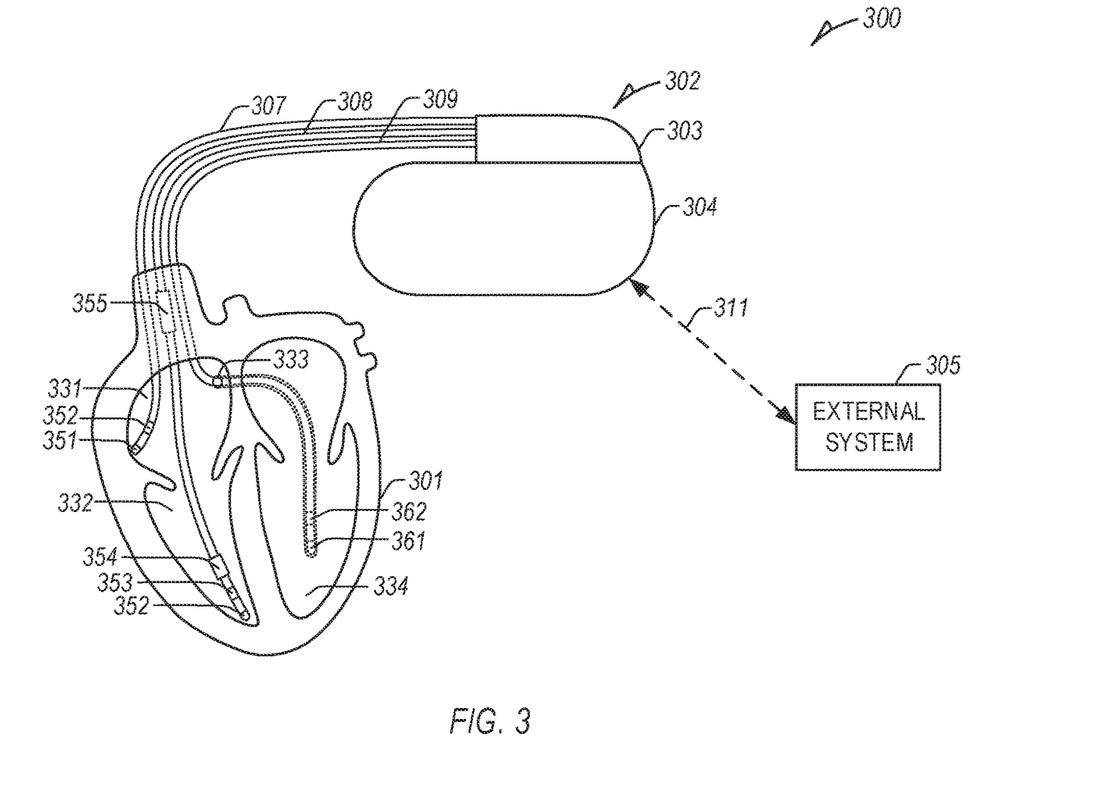
FIG. 3 illustrates an example of a Cardiac Rhythm Management (CRM) system and portions of an environment in which the CRM system can operate.

FIG. 3 illustrates an example of a Cardiac Rhythm Management (CRM) system 300 and portions of an environment in which the CRM system 300 can operate. The CRM system 300 can include an ambulatory medical device, such as an implantable medical device (IMD) 302 that can be electrically coupled to a heart 301 through one or more leads, such as one or more of a first, second, or third lead 307-309 coupled to the IMD 302 using a header 303, and an external system 305 that can communicate with the IMD 302, such as via a communication link 311.

The IMB 302 can include an implantable cardiac device, such as a pacemaker, an implantable cardioverter-defibrillator (ICD), or a cardiac resynchronization therapy defibrillator (CRT-D). The IMB 302 can include one or more monitoring or therapeutic devices, such as a subcutaneous implanted device, a wearable external device, a neural stimulator, a drug delivery device, a biological therapy device, or one or more other ambulatory medical devices. The IMD 302 may be coupled to or substituted by a monitoring medical device, such as a bedside or other external monitor.

The IMB 302 can include a hermetically sealed CAN 304 that can house an electronic circuit that can sense a physiologic signal in the heart 301 and can deliver one or more therapeutic electrical pulses to a target region, such as in the heart, through the one or more leads. In certain examples, the CRM system 300 can include only a single lead (e.g., the second lead 308, etc.), only two leads (e.g., the first and second leads 307, 308), or three or more leads, etc.

The first lead 307 can include a proximal end that can be configured to be connected to the IMD 302 and a distal end that can be configured to be placed at a target location, such as in the right atrium (RA) 331 of the heart 301. The first lead 307 can have a first pacing-sensing electrode 351 that can be located at or near its distal end, and a second pacing-sensing electrode 352 that can be located at or near the first pacing-sensing electrode 351. The first and second pacing-sensing electrodes 351, 352 can be electrically connected to the IMD 310, such as via separate conductors in the first lead 307, such as to allow for sensing of the right atrial activity and optional delivery of atrial pacing pulses.

The second lead 308 can be a defibrillation lead that can include a proximal end that can be connected to the IMD 310 and a distal end that can be placed at a target location, such as in the right ventricle (RV) 332 of the heart 301. The second lead 308 can have a first pacing-sensing electrode 352 that can be located at distal end, a second pacing-sensing electrode 353 that can be located near the first pacing-sensing electrode 352, a first defibrillation coil electrode 354 that can be located near the electrode 353, and a second defibrillation coil electrode 355 that can be located at a distance from the distal end, such as for superior vena cava (SVC) placement. The electrodes 352-355 can be electrically connected to the IMD 302, such as via separate conductors in the second lead 308. The first and second pacing-sensing electrodes 352, 353 can allow for sensing of a ventricular electrogram and can optionally allow delivery of one or more ventricular pacing pulses, and the first and second defibrillation coil electrodes 354, 355 can allow for delivery of one or more ventricular cardioversion/defibrillation pulses.

In an example, the second lead 308 can include only three electrodes. The first pacing-sensing electrode 352 and the first defibrillation coil electrode 354 can be used for sensing or delivery of one or more ventricular pacing pulses, and the electrodes the first defibrillation coil electrode 354 and the second defibrillation coil electrode 355 can be used for delivery of one or more ventricular cardioversion or defibrillation pulses.

The third lead 309 can include a proximal end that can be connected to the IMD 302 and a distal end that can be configured to be placed at a target location, such as in a left ventricle (LV) 334 of the heart 301. The third lead 309 may be implanted through the coronary sinus 333 and may be placed in a coronary vein over the LV, such as to allow for delivery of one or more pacing pulses to the LV. The third lead 309 can include a first distal electrode 361 that can be located at a distal end of the third lead 309 and a second distal electrode 362 that can be located near the first distal electrode 361. The first and second distal electrodes 361, 362 can be electrically connected to the IMD 302, such as via separate conductors in the third lead 309, such as to allow for sensing of the LV electrogram and optionally allow delivery of one or more resynchronization pacing pulses from the LV.

The IMD 302 can include an electronic circuit that can sense a physiologic signal. The physiologic signal can include an electrogram or a signal representing mechanical function of the heart 301. The hermetically sealed CAN 304 may function as an electrode, such as for sensing or pulse delivery. For example, an electrode from one or more of the first, second, or third leads 307-309 may be used together with the CAN 304, such as for unipolar sensing of an electrogram or for delivering one or more pacing pulses. A defibrillation electrode from the second lead 308 may be used together with the CAN 304, such as for delivering one or more cardioversion/defibrillation pulses.

In an example, the IMD 302 can sense impedance, such as between electrodes located on one or more of the first, second, or third leads 307-309 or the CAN 304. The IMD 302 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 302 can be configured to inject current between an electrode on the second lead 308 and the CAN 304, and to sense the resultant voltage between the same electrodes or between a different electrode on the second lead 308 and the CAN 304. A physiologic signal can be sensed from one or more physiologic sensors that can be integrated within the IMB 302. The IMD 302 can also be configured to sense a physiologic signal from one or more external physiologic sensors or one or more external electrodes that can be coupled to the IMB 302. Examples of the physiologic signal can include one or more of heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the subject and the capability of the implantable device, other arrangements and uses of these leads and electrodes are anticipated and included herein.

The external system 305 can allow for programming of the IMB 302 and can receives information about one or more signals acquired by IMD 302, such as can be received via a communication link 311. The external system 305 can include a local external IMB programmer. The external system 305 can include a remote patient management system that can monitor patient status or adjust one or more therapies, such as from a remote location.

The communication link 311 can include one or more of an inductive telemetry link, a radio-frequency telemetry link, or a telecommunication link, such as an internet connection. The communication link 311 can provide for data transmission between the IMB 302 and the external system 305. The transmitted data can include, for example, real-time physiologic data acquired by the IMD 302, physiologic data acquired by and stored in the IMD 302, therapy history data or data indicating IMD operational status stored in the IMD 302, one or more programming instructions to the IMD 302, such as to configure the IMB 302 to perform one or more actions that can include physiologic data acquisition, such as using programmably specifiable sensing electrodes and configuration, device self-diagnostic test, or delivery of one or more therapies.

Portions of the IMB 302 or the external system 305 can be implemented using hardware, software, or any combination of hardware and software. Portions of the IMD 302 or the external system 305 may be implemented using an application-specific circuit that can be constructed or configured to perform one or more particular functions or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 302, the CRM system 500 could include a subcutaneous medical device (e.g., subcutaneous ICD, subcutaneous diagnostic device), wearable medical devices (e.g., patch-based sensing device), or other external medical devices.

Figure 4:
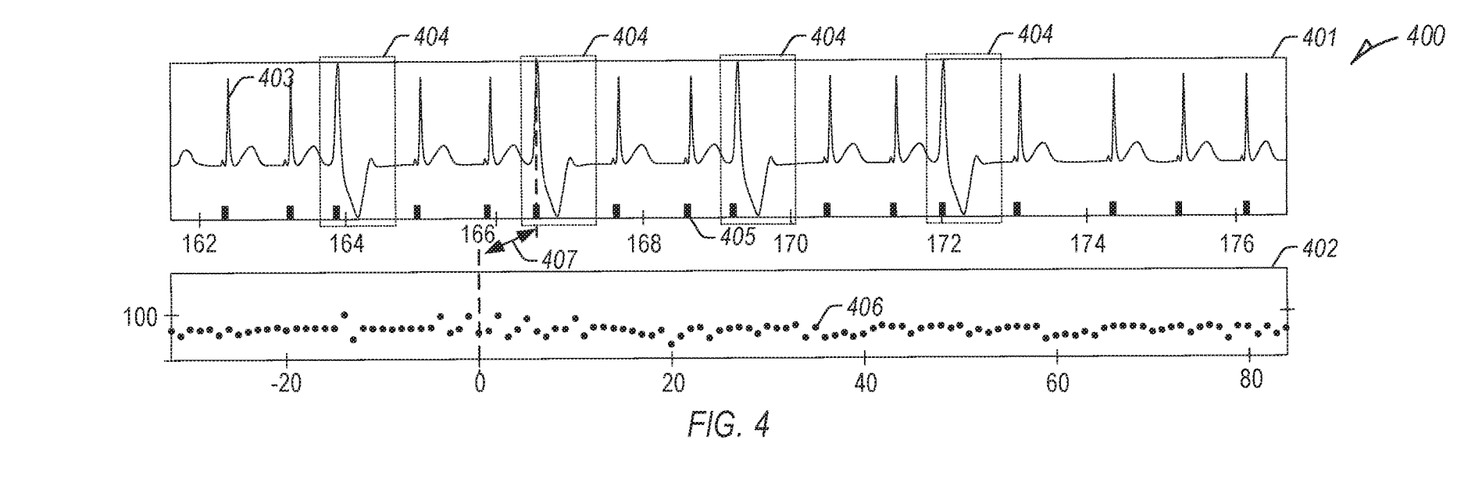
FIGS. 4-5 illustrate example episodes including PVCs.
Figure 5:
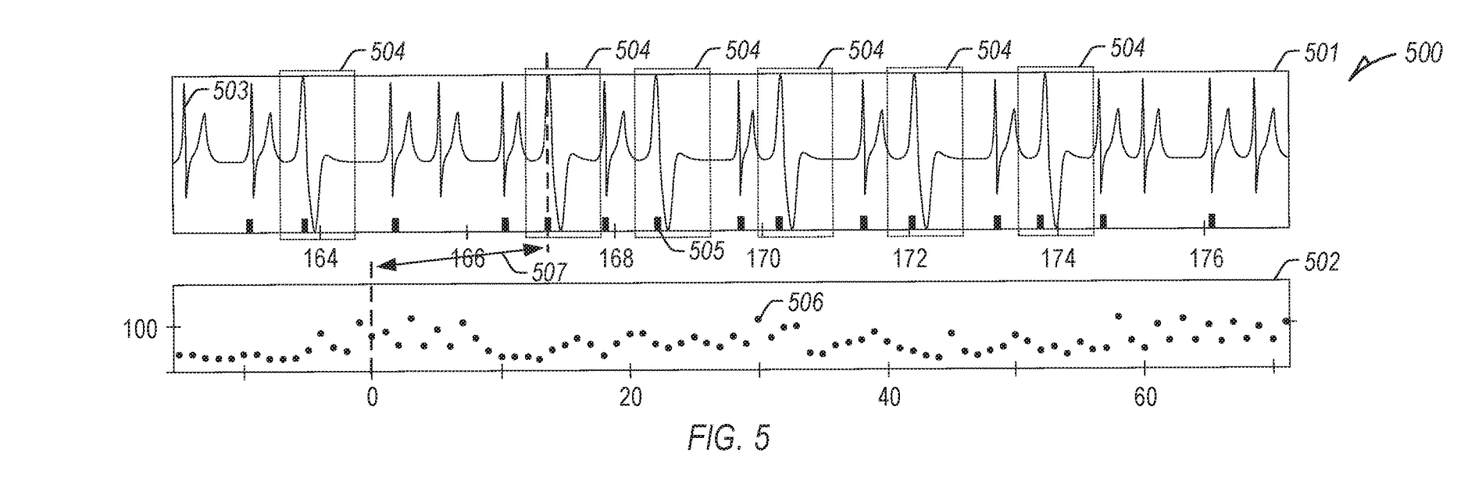

FIGS. 4-5 illustrate example episodes 400, 500 including PVCs. FIG. 4 illustrates generally an example episode 400 of AF that was rejected due to PVCs using a prior art AF detection algorithm, and FIG. 5 illustrates generally an example episode 500 of a false positive AF classification due to PVCs using a prior art AF detection algorithm.

The example episodes 400, 500 include cardiac electric signals 401, 501 and corresponding rate distributions 402, 502. Normal depolarizations are illustrated in the cardiac electrical signals 401, 501 without boxes, such as first depolarizations 403, 503. The cardiac electrical signals 401, 501 illustrate time on the horizontal axis in seconds (e.g., 162-176, etc.) and a vertical axis represents a normalized magnitude of the cardiac electrical signals 401, 501, such as detected by a cardiac sensor (e.g., an electrocardiogram detected by one or more electrodes, etc.).

In an example, PVCs can be detected, for example, using one or more of rate, morphology, amplitude, or frequency information of a cardiac electrical signal. In certain examples, PVCs can be detected as wide QRS complex, wider than a normal or expected depolarization (e.g., the first depolarization 403, etc.). In FIG. 4, four PVCs 404 are detected in the cardiac electrical signal 401. In FIG. 5, six PVCs 504 are detected in the cardiac electrical signal 501. Ventricular events are illustrated with markers 405, 505 in each of the cardiac electrical signals 401, 501.

The rate distributions 402, 502 illustrate an index of individual rates of ventricular events, including ventricular events 406, 506 of the cardiac electrical signals 401, 501, syncing at origins 407, 507, on the horizontal axis and a vertical axis representing heart rate. In certain examples, AF can be detected using the rate distributions 402, 502, such as characteristics of the rate distributions, including intervals between successive events, classification or categorization of the different intervals, etc. In an example, candidate AF events can be detected, and then classified as an AF event or a non-AF event using one or more other circuits, methods, or confirmation using previous, subsequent, or additional information.

Figure 6:
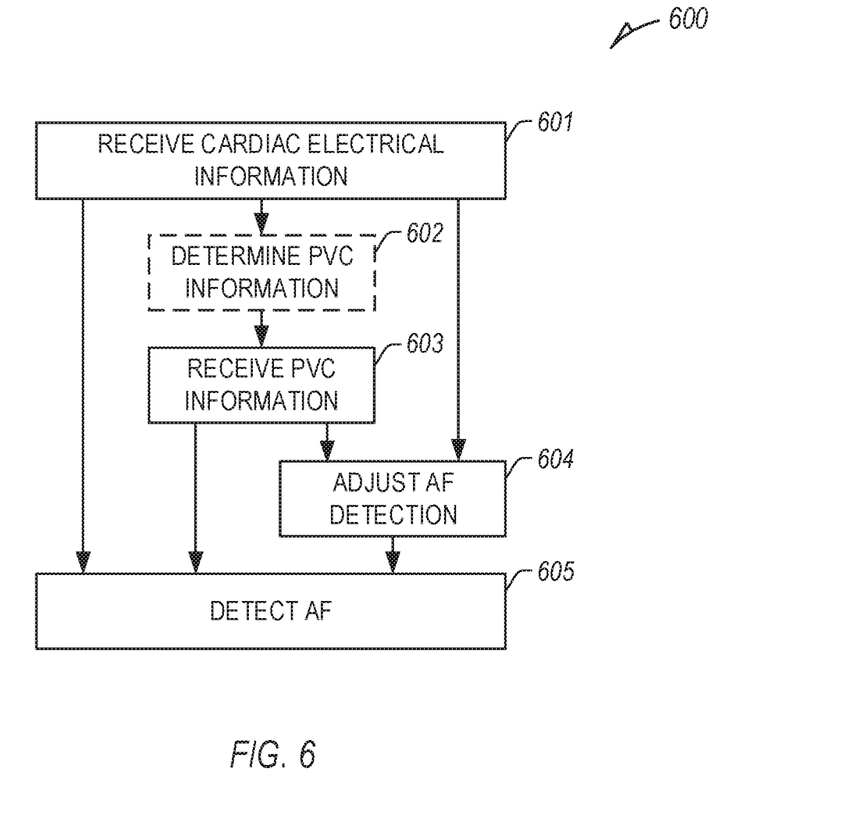
FIG. 6 illustrates generally an example method including detecting AF of a subject.

FIG. 6 illustrates generally an example method 600 including detecting AF of a subject. In an example, detecting AF can including detecting candidate AF events, and in certain examples, classifying the candidate AF events as AF or non-AF.

At 601, cardiac electrical information is received, such as using a signal receiver circuit of a component of a medical system, such as a first ambulatory medical device, a medical device programmer, etc. The cardiac electrical information can be received from a cardiac sensor or one or more other devices (e.g., a second ambulatory medical device, etc.).

At 602, PVC information is optionally determined, such as by a first assessment circuit using the received cardiac electrical information. In an example, one or more PVC events can be determined of a subject, such as using the received cardiac electrical information (e.g., a morphology, a rate, a magnitude, a frequency, or one or more other characteristics or a comparison to one or more templates or previous cardiac electrical information, etc.). In an example, determining PVC information can include determining a PVC state of the subject, such as using one or more detected PVC events, their proximity, the number of detected PVC events in a specific number of cardiac cycles, etc.

At 603, PVC information can be received, such as from the first assessment circuit or one or more other devices (e.g., the second ambulatory medical device, etc.) using the signal receiver circuit. In an example, the PVC information can include a determination of one or more PVC states, including, for example, separate low, high, and very-high PVC states, or one or more other determinations of different PVC states of the subject, etc.

At 604, AF detection can be adjusted using the received PVC information, such as using one or more determined PVC events or states of the subject. In an example, an assessment circuit can adjust AF detection using the received PVC information. The assessment circuit can count a number of detected PVC events in a first time period, such as a first detection window, etc., and determine a PVC state of the subject using the count of PVC events in the first time period. The AF detection can be adjusted using the determined PVC state.

For example, a first AF detection mode (e.g., a low-PVC burden mode) can tolerate a first number of PVC events (e.g., below 30% of cardiac intervals as PVC events, etc.). The assessment circuit can determine a low-PVC state if the PVC event count is below a first threshold, such as in a specific detection window, etc., and use the low-PVC burden mode to detect AF, such as using one or more of the AF detection algorithms described above, even in detection window having the first number of PVC events.

In a second AF detection mode (e.g., a high-PVC burden mode) can remove detected PVC events, for example, from a detection window. Once removed from the detection window, AF detection can proceed on the remaining cardiac electrical information (e.g., beats or intervals) in the window. In an example, the detection algorithm, in the context of the remaining cardiac electrical information, can remain the same as in the first AF detection mode, but the information being considered has been altered. However, the threshold for individual beats or intervals to remain in the window for consideration increases, as in this mode, more intervals are removed from the detection window. The assessment circuit can determine a high-PVC state if the number of PVC events is above the first number of PVC events (e.g., at or above 30% of cardiac intervals as PVC events, etc.), such as in a specific detection window, etc. In certain examples, the beats or intervals before, after, or both before and after the detected PVC event can be removed from the detection window as well, and AF detection can proceed on the remaining cardiac electrical information in the window.

AF detection can be suspended in a third AF detection mode if the number of PVC events is above a second number of PVC events (e.g., at or above 70% of the cardiac intervals as PVC events, etc.), such as in a specific detection window, etc. In an example, one or more other thresholds can be used. Further, in certain examples, when AF detection is suspended or disabled, an alert can be issued or provided that AF classification has been suspended. Suspending AF in the third AF detection mode can reduce power consumption of the device, as the number and amount of PVCs may make it difficult to detect a condition with confidence outside of the PVCs themselves.

In other examples, the PVC burden or state can be determined, or an indication of the PVC burden or state can be received, such as from a user or one or more other processes. In other examples, adjusting AF detection can include adjusting AF classification, such that candidate AF events are detected, but one or more classification parameters or thresholds of such detected AF events can change. In other examples, AF detection parameters can include rate thresholds (e.g., rates above or below upper or lower thresholds are not considered as valid beats or intervals for AF detection), sequential rate or interval change thresholds between successive or ordered beats or intervals, etc.

Figure 7:
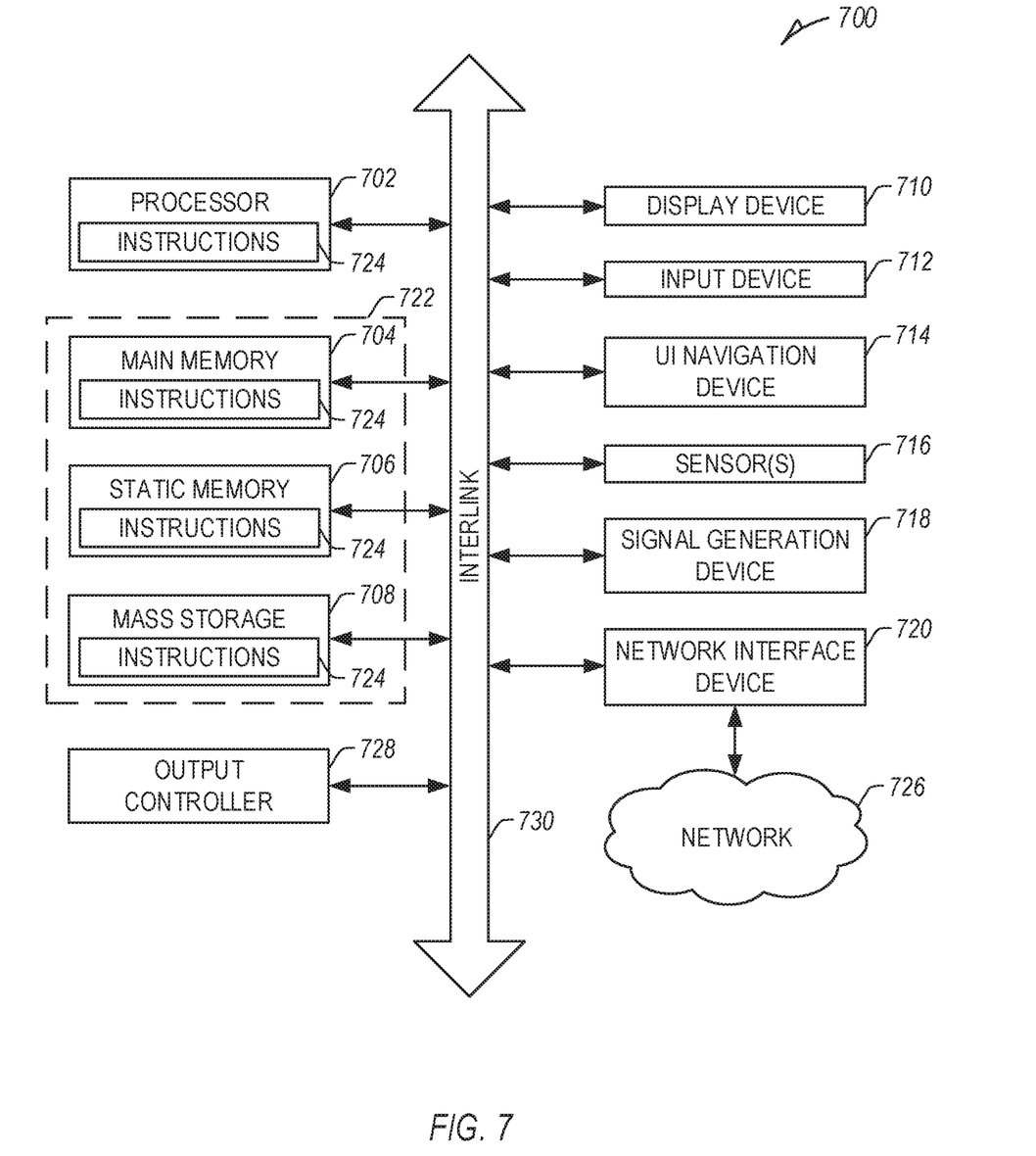
FIG. 7 illustrates a block diagram of an example machine upon which any one or more of the techniques discussed herein may perform.

FIG. 7 illustrates a block diagram of an example machine 700 upon which any one or more of the techniques (e.g., methodologies) discussed herein may perform. Portions of this description may apply to the computing framework of one or more of the medical devices described herein, such as the IMD, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 700. Circuitry (e.g., processing circuitry) is a collection of circuits implemented in tangible entities of the machine 700 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 700 follow.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 700 may include a hardware processor 702 (e.g., a central processing unit (CPU), a graphics processing unit (GPU), a hardware processor core, or any combination thereof), a main memory 704, a static memory (e.g., memory or storage for firmware, microcode, a basic-input-output (BIOS), unified extensible firmware interface (UEFI), etc.) 706, and mass storage 708 (e.g., hard drive, tape drive, flash storage, or other block devices) some or all of which may communicate with each other via an interlink (e.g., bus) 730. The machine 700 may further include a display unit 710, an alphanumeric input device 712 (e.g., a keyboard), and a user interface (UI) navigation device 714 (e.g., a mouse). In an example, the display unit 710, input device 712, and UI navigation device 714 may be a touch screen display. The machine 700 may additionally include a signal generation device 718 (e.g., a speaker), a network interface device 720, and one or more sensors 716, such as a global positioning system (GPS) sensor, compass, accelerometer, or one or more other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 702, the main memory 704, the static memory 706, or the mass storage 708 may be, or include, a machine-readable medium 722 on which is stored one or more sets of data structures or instructions 724 (e.g., software) embodying or utilized by any one or more of the techniques or functions described herein. The instructions 724 may also reside, completely or at least partially, within any of registers of the processor 702, the main memory 704, the static memory 706, or the mass storage 708 during execution thereof by the machine 700. In an example, one or any combination of the hardware processor 702, the main memory 704, the static memory 706, or the mass storage 708 may constitute the machine-readable medium 722. While the machine-readable medium 722 is illustrated as a single medium, the term "machine-readable medium" may include a single medium or multiple media (e.g., a centralized or distributed database, and/or associated caches and servers) configured to store the one or more instructions 724.

The term "machine-readable medium" may include any medium that is capable of storing, encoding, or carrying instructions for execution by the machine 700 and that cause the machine 700 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may be further transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 700, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
    a signal receiver circuit configured to receive cardiac electrical information and premature ventricular contraction (PVC) information of a subject; and
    an assessment circuit configured to:
        detect, using the received cardiac electrical information, atrial fibrillation (AF) of the subject using one of multiple AF detection modes, each of the multiple AF detection modes configured to detect AF of the subject;
        determine a count of PVC events in a first detection window using the received PVC information from the first detection window; and
        transition between different first and second AF detection modes of the multiple AF detection modes-based on the determined count of PVC events in the first detection window.

2. The system of claim 1, wherein the assessment circuit is configured to determine a PVC state of the subject using the determined count of PVC events in the first detection window and to transition between the different first and second AF detection modes based on the determined PVC state.

3. The system of claim 1, wherein the received PVC information comprises an indication of a detected PVC event.

4. The system of claim 1, wherein, if the PVC event count is below a first threshold, the assessment circuit is configured to determine a low-PVC state, and the system is configured to detect AF of the subject using a low-PVC burden mode,
    wherein, if the PVC event count meets or exceeds the first threshold, the medial-device system is configured to determine a high-PVC state, and the system is configured to detect AF of the subject using a high-PVC burden mode, and
    wherein the first threshold is more than two detected PVC events in the first detection window.

5. The system of claim 4,
    wherein, to adjust the AF detection in the high-PVC burden mode, the assessment circuit is configured to remove cardiac electrical information associated with the detected PVC events from the first detection window, and to detect AF in the first detection window using the remaining cardiac electrical information in the first detection window, and
    wherein the assessment circuit is configured to detect AF of the subject in the first detection window using the remaining cardiac electrical information from the first detection window.

6. The system of claim 5, wherein, to adjust the AF detection in the high-PVC burden mode, the assessment circuit is configured to remove cardiac electrical information associated with the detected PVC events, and cardiac electrical information from a cardiac interval at least one of preceding or proceeding cardiac intervals of the detected PVC events from the first detection window.

7. The system of claim 1 wherein, if the PVC event count is below a first threshold, the assessment circuit is configured to determine a low-PVC state, and the assessment circuit is configured to detect AF of the subject using a low-PVC burden mode in the first detection window, wherein, if the PVC event count meets or exceeds the first threshold, but is below a second threshold higher than the first threshold, the medial-device system is configured to determine a high-PVC state, and the assessment is configured to detect AF of the subject using a high-PVC burden mode in the first detection window, and wherein, if the PVC event count meets or exceeds the second threshold, the system is configured to suspend AF detection in the first detection window.

8. The system of claim 1, wherein the assessment circuit is configured to control storage of received cardiac electrical information for the first detection window using the received PVC information.

9. A method, comprising:
receiving cardiac electrical information and premature ventricular contraction (PVC) information of a subject using a signal receiver circuit;
detecting, using an assessment circuit and the received cardiac electrical information, atrial fibrillation (AF) of the subject using one of multiple AF detection modes, each of the multiple AF detection modes configured to detect AF of the subject;
determining a count of PVC events in a first detection window using the received PVC information from the first detection window; and
transitioning, using the assessment circuit, between different first and second AF detection modes of the multiple AF detection modes based on the determined count of PVC events in the first detection window.

10. The method of claim 9, comprising:
determining, using the assessment circuit, a PVC state of the subject using the determined count of PVC events in the first detection window and transitioning between the different first and second AF detection modes based on the determined PVC state.

11. The method of claim 9, comprising:
detecting, using the assessment circuit, a PVC event using the received PVC information,
wherein determining the count of PVC events in the first detection window comprises counting, using the assessment circuit, detected PVC events in the first detection window.

12. The method of claim 9, comprising:
determining, using the assessment circuit, a PVC state of the subject using the count of the PVC events in the first detection window,
wherein determining the PVC state of the subject comprises determining:
a low-PVC state if the PVC event count is below a first threshold; and
a high-PVC state if the PVC event count meets or exceeds the first threshold, but is below a second threshold, and
wherein detecting AF of the subject includes using:
a low-PVC burden mode if the PVC event count is below the first threshold; and
a high-PVC burden mode if the PVC event count meets or exceeds the first threshold, but is below the second threshold.

13. The method of claim 12, comprising:
suspending AF detection in the first detection window if the PVC event count meets or exceeds the second threshold higher than the first threshold; and
providing a notification, using the assessment circuit, that the AF detection has been suspended.

14. The method of claim 12, wherein detecting AF comprises detecting an AF episode in the first detection window using the received cardiac electrical information in the first detection window, and
wherein, in the high-PVC burden mode, adjusting AF detection comprises removing cardiac electrical information associated with the detected PVC events from the first detection window and detecting AF in the first detection window using the remaining cardiac electrical information in the first detection window.

15. The method of claim 14, wherein, in the high-PVC burden mode, adjusting AF detection comprises removing cardiac electrical information associated with the detected PVC events and cardiac electrical information from a cardiac interval at least one of preceding or proceeding cardiac intervals of the detected PVC events from the first detection window.

16. A system, comprising:
a signal receiver circuit configured to receive cardiac electrical information and premature ventricular contraction (PVC) information of a subject; and
an assessment circuit configured to:
detect atrial fibrillation (AF) of the subject using the received cardiac electrical information of the subject;
determine a count of PVC events in a first detection window using the received PVC information from the first detection window;
determine a PVC state of the subject using the determined count of PVC events in the first detection window, including to:
if the PVC event count is below a first threshold, determine a low-PVC state; and
if the PVC event count meets or exceeds the first threshold, determine a high-PVC state; and
adjust the AF detection for the first detection window based on the determined PVC state, including to:
detect AF of the subject in the first detection window using a low-PVC burden mode in the low-PVC state; and
detect AF of the subject in the first detection window using a high-PVC burden mode in the high-PVC state, wherein an AF detection threshold is different in the high-PVC burden mode than in the low-PVC burden mode.

17. The system of claim 16, wherein the assessment circuit is configured to suspend AF detection in the first detection window if the PVC event count in the first detection window meets or exceeds a second threshold higher than the first threshold.

18. The system of claim 16,
wherein, to adjust the AF detection in the high-PVC burden mode, the assessment circuit is configured to remove cardiac electrical information associated with the detected PVC events from the first detection window and cardiac electrical information from a cardiac interval at least one of preceding or proceeding cardiac intervals of the detected PVC events from the first detection window, and
wherein the assessment circuit is configured to detect AF of the subject in the first detection window using the remaining cardiac electrical information from the first detection window.

19. The system of claim 16, wherein the first threshold is based on a percentage of detected cardiac intervals in the first detection window, and
wherein the first detection window is a time period.

20. The system of claim 16, wherein the first detection window is a number of detected cardiac intervals.

* * * * *